United States Patent [19]

Amstutz et al.

[11] Patent Number: 4,559,013
[45] Date of Patent: Dec. 17, 1985

[54] ORTHODONTIC SHIELD, ORTHOTIC DEVICE AND MUSICIAN EMBOUCHURE AID AND METHOD OF PRODUCING AND USING SAME

[76] Inventors: A. Keith Amstutz, 1700 Senate St., Columbia, S.C. 29201; Bruce H. Kinnie, 2301 Kneece Rd., Columbia, S.C. 29206

[21] Appl. No.: 496,910

[22] Filed: May 23, 1983

[51] Int. Cl.⁴ .............................................. A61C 7/00
[52] U.S. Cl. ........................................ 433/22; 433/6; 433/8
[58] Field of Search ............... 128/132 R, 136; 433/5, 433/6, 8, 9, 22

[56] References Cited

U.S. PATENT DOCUMENTS

| | | | |
|---|---|---|---|
| 2,843,555 | 7/1958 | Berridge | 128/136 X |
| 2,919,693 | 1/1960 | Ross | 128/136 |
| 2,999,077 | 9/1961 | Nitzsche et al. | 128/136 X |
| 3,224,443 | 12/1965 | Monaghan | 128/136 |
| 4,063,552 | 12/1977 | Going et al. | 128/136 |
| 4,180,912 | 1/1980 | Kesling | 433/8 X |
| 4,457,708 | 7/1984 | Dufour | 433/6 |
| 4,512,740 | 4/1985 | Kurz | 433/8 X |

Primary Examiner—George F. Lesmes
Assistant Examiner—Nancy A. B. Swisher
Attorney, Agent, or Firm—B. C. Killough

[57] ABSTRACT

This invention relates to orthodontic shields, orthotic devices, and musician embouchure aids and the method of producing and using same, and specifically relates to the use of medical silicone to produce a shield which may be used in conjunction with orthodontic aids and appliances, and to produce an orthotic device which may be used to lessen and relieve temporomandibular joint syndrome.

12 Claims, 10 Drawing Figures

ORTHODONTIC SHIELD, ORTHOTIC DEVICE AND MUSICIAN EMBOUCHURE AID AND METHOD OF PRODUCING AND USING SAME

BACKGROUND OF THE INVENTION

This invention relates to the use of a room temperature setting medical silicone composition to produce an orthodontic or orthotic device which may be used to lessen irritation and misalignment in and around the mouth and lips, and particularly may be used as an embouchure aid for wind instrumentalists who wear braces or other orthodontic devices and further may be particularly used to relieve temporomandibular joint syndrome.

Braces and similar orthodontic devices have long been a problem for wind instrumentalists. They are a constant source of mental and physical irritation to wearers who are players of brass or windwood instruments. Additionally, these orthodontic protrusions on the teeth have a negative effect on the embouchure (playing position of the lips) and performance flexibility for wind instrumentalists.

In the brass instrument family, the mouthpiece rests directly on the lips, and the tone is produced by a stream of air vibrating the lips at frequencies from roughly 60 cps to 2400 cps. Lateral mouthpiece pressure is required to contain the vibrating lips and provide a seal to prevent air from leaking around the embouchure. The reuslting combination of vibration and pressure applied directly to the orthodontic appliance causes considerable irritation to the soft lip tissue accompanied by physical discomfort at times to the point where concentration or performance is impossible.

The woodwind family of instruments utilizes the projection of an air column over an open hole or through a single or double reed which vibrates to produce the sound. In positioning the lips to control the air flow, muscle tension is required to hold the lips in position. With the single and double reeds, the reed or mouthpiece is inserted between the teeth and the lips must grip in a circular pattern to prevent air leakage. In both situations, any sharp protrusions from orthodontic devices are a source of irritation and pain. Since the problem of orthodontics may involve a large percentage of the participants in an instrumental music program, music educators, parents, scientists, and students are constantly searching for means to lessen the inconvenience and discomfort experienced during instrumental music performance.

The prior art consists of the use of a strip of chamois or other cloth, wax, or plastic dental shield. The chamios or cloth is inserted between the teeth and lip tissue, but as soon as the embouchure is adjusted for a register change or a quick breath, the chamois tends to slip and disturb either the embouchure or the air column. If the same piece of chamois or cloth is used for a period of time, it adopts a distinctive aroma and, no doubt, has a negative effect on oral hygiene.

Pliable wax, cut into a thin strip, which is pressed around the braces to smooth over the sharp edges, has also been used. After applying the wax strips, the student must spend several minutes adjusting and softening the wax to obtain a reasonable level of adaptability to his embouchure. By the end of a performance the braces have cut through the wax and the student must pick the wax residue from around the teeth and appliance only to face a repeat of this tedious routine at the next practice session. The use of wax does not facilitate easy maintenance, and, correspondingly, does not facilitate oral hygiene.

Thermoplastic teeth protectors have also been used. These are form fitted to the teeth with a ridge at the back to assist in insertion and removal. This device is convenient and reusable, but requires frequent replacement as the teeth change position in response to treatmet by the braces or othodontic device also resulting in a slightly altered teeth aperture. In an area where minimal change can have drastic effects on performance response, any artificial alteration of the teeth aperture is not desirable. The performer may be required to spend an additional period of adustment after each routine the orthodontic adjustment has been completed. Thermoplastic protectors are also expensive.

Sports which require any physical exertion or contact are sources of lip and oral irritation and possible dental damage, both for those who wear orthodondic appliances and those who do not. Even in supposed non-contact sports such as basketball and volleyball, there is a risk of injury which is heightened by the presence of braces or other orthodontic devices. The prior art does not presently provide a mouth protector which may easily and inexpensively be custom fit to the athlete-wearer.

Temporomandibular Joint (TMJ) Syndrome is an organic disorder which can result in pain of the eye, head, face, teeth, gums, jaws, ears, throat, neck, shoulder, and back. TMJ Syndrome is found when the lower jaw is misaligned with the face and upper jaw. When TMJ Syndrome exists, the upper and lower teeth meet incorrectly, such as when the mouth is tightly closed or during chewing, and a misalignment of the lower jaw result in abnormal pressures on the TMJ and supporting muscles. This pressure or stress on the TMJ further results in pain in distant-referred parts of the body. The prior art has consisted of custom-made, expensive orthotic devices which hold the teeth apart to prevent misalignment pressure on the TMJ. These devices cost approximately $400.00 to $2,000.00 to make and fit, including professional fees and charges. The cost usually prohibits this device from being used as a diagnostic aid.

An improvement on the original Rocobado appliance is the orthopedic head reposturing appliance (OHPA). This orthopedic device contacts the back of the head, comes around the face, and puts pressure on the face either on the upper lip, just below the nose. Great discomfort arises where the device contacts this thin nose area. The prior art does not provide a method or aparatus which will formfit the users device, yet which will alleviate discomfort.

An object of the invention is to provide an orthodontic shield and/or embouchure aid which will shield the mouth and lips from braces and other irritations, while still allowing proper embouchure while playing wind instruments.

Another object of the invention is to provide a orthodontic shield, orthotic device, and embouchure aid which is reusable yet inexpensive.

Yet another object of the invention is to provide an orthodontic shield, orthotic device, and embouchure aid which may be inexpensively fit to the user's particular mouth.

Still another object of the invention is to provide aan orthodontic shield, orthotic device, and embouchure aid which promotes proper oral hygiene.

Still a further object of the invention is to provide an orthodontic shield and embouchure aid which will not leave residue in the mouth.

Yet a further object of the invention is to provide an orthodontic shield and embouchure aid which will function properly even in view of critical dimensional tolerances.

Yet still a further object of the invention is to provide an orthotic device to relieve Temporomandibular Joint Syndrome.

Still yet a further object of the invention is to provide an orthotic device for relieving Temporomandibular Joint Syndrome which may be prepared by the user.

Still an additional object of the invention is to provide an orthotic device which may be cost-effectively used as a diagnostic aid.

Still yet another object of the invention is to provide a cushion which may be used in conjunction with an orthopedic head reposturing device to eliminate discomfort where the device contacts the wearer's face.

Yet still an additional subject of the invention is to provide a low cost, custom fit shield to protect the wearer's teeth and orthodontic aids from injury due to impact.

SUMMARY OF THE INVENTION

This invention provides an apparatus which may be used as an oral shield and as a musician's embouchure aid. The shield is produced by taking room temperature setting medical silicone, which is suitable for oral application, and preparing it for use. The composition is placed in the mouth, so that it fully and adequately covers braces or other sources of oral irritation. The composition is allowed to set, and is then removed from the mouth. The composition, now in its set form and molded to the shape of the user's teeth, mouth, and orthodontic aids, is trimmed using a knife or other sharp object. The resulting device then may be used as a suitable shield for teeth, braces, and the like from the mouth and mouth sores, while still allowing proper embouchure. The device is custom fit, relatively inexpensive, and may be reused several times.

Lingual appliances, which are in the nature of braces applied to the inside of the teeth so that they are not visible, result in pain and injury to the wearer through cuts and abrasions to the tongue. By preparing a shield as described herein, damage and injury to the tongue may be eliminated.

The method and device may also be used to provide a protective shield to protect the mouth, teeth, and dental appliances from damage due to impact, such as that incurred while engaging in physical sports and activities. By using the method described herein, a reusable device can be produced which can provide an effective shield that may be custom molded to the mouth, teeth, and orthodontic appliances of the wearer.

Temporomandibular Joint Syndrome may be relieved by preparing the medical silicone for use and placing it in the mouth over the lower teeth in such a manner as to keep the teeth slightly apart. By completely covering the back three or four teeth in the mouth, the undercut of the teeth holds the medical silicone in place, and also holds the teeth apart so that the misalignment of the lower jaw with the upper jaw does not place pressure upon the temporomandibular joint. This orthotic device is reusable and may be constructed in such a manner so that it is in one piece. Replacement may be accomplished easily and by the user.

Cervical traction devices aggravate temporomandibular joint syndrome in those people who are predisposed to TMJ syndrome. Cervical traction devices place a lifting pressure on the head by applying force to the chin and the back of the head. This pressure on the chin may result in up to twenty pounds additional pressure on the temporomandibular joint. This resulting pressure creates and aggravates temporomandibular joint pain and dysfunction. By using the method and device as described herein in conjunction with cervical traction, the problem associated with cervical traction devices and temporomandibular joint syndrome are lessened.

The method and device may further be used to produce a cushion for use in conjunction with orthopedic devices such as the orthopedic head reposturing appliance for the correction of underbite or overbite. The same method is used to produce the cushion as is described herein by placing the medical silicone on the device allowing it to set while in contact with the user's face at the thin nose area, then particularly trimming the medical silicone to the desired size to produce the completed apparatus.

Also, by using the method and device as described herein, a shield may be produced which will protect the teeth and orthodontic aids from impact or injury. An inexpensive shield can be produced which is formfit to the particular user's mouth and which may be reused several times, while being relatively inexpensive and comparable in cost to existing mouth guards or shields which are not custom fit to the user's mouth.

DESCRIPTION OF THE DRAWINGS

These and other objects, advantages and features of the invention will become apparent to those skilled in the art when taken in connection with the accompanied drawings and detailed description, wherein.

DETAILED DESCRIPTION OF PREFERRED EMBODIMENT(S)

Figure 1:
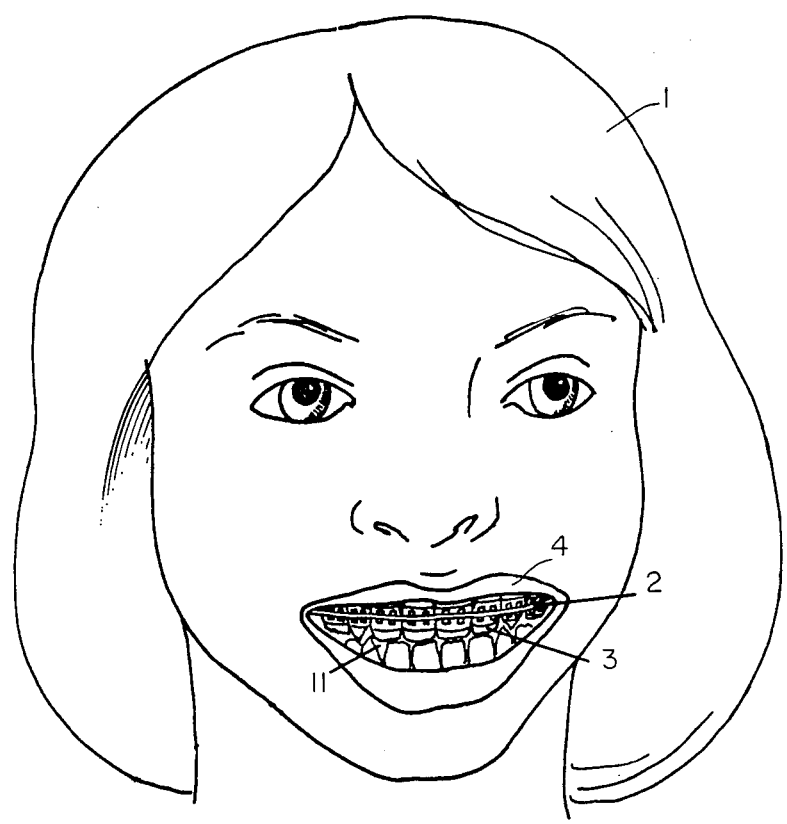
FIG. 1 is a view of a wearer of braces.

This invention relates to the use of a room setting medical silicone, which may be an organo polysiloxane having vinyl groups, to relieve irritation which is associated with the mouth, and particularly, with orthodontic aids. FIG. 1 shows a person 1 wearing braces 2 on the upper teeth 3. If the upper lip 4 is lowered over the braces 2, and the wearer places muscle tension on the upper lip 4, such as is incurred with the playing of musical instruments, the metal braces cut into the lip, causing discomfort and soreness.

Figure 2:
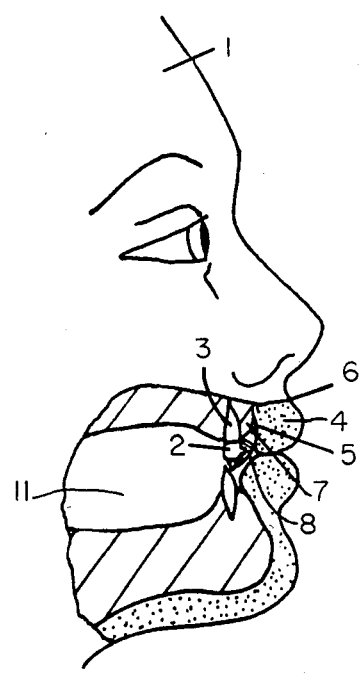
FIG. 2 is a partially sectioned view showing a wearer of braces with the orthodontic shield in place, prior to trimming of the shield.

The room temperature setting medical silicone is first prepared for use. Typically, this will be a two part medical silicone, such as the very high viscosity polyvinyl silicone manufactured by Healthco, or Exaflex[1], which is a medical silicone composition comprising generally an organovinylpolysiloxane, an organo hydrogen polysiloxane, a catalyst for promoting an addition reaction therebetween, hydrophobic fillers and finely divided paladium and/or an alloy thereof. This composition is more fully described in U.S. Pat. No. 4,273,902. The two part compositions of base and catalyst are mixed in equal porportions for approximately thirty (30) seconds. The composition is then prepared in a strip which is larger than the brace area, and is placed into the mouth 11 over the teeth 3 and braces 2 and between the inside of the lip 5 and the teeth 3 and braces 2, as is shown in FIG. 2. By rubbing with a finger on the outside of the upper lip area 6, the composition can be spread over the teeth 3 to completely cover the brace area 2, and to assure a smooth fit with the gum 7 and inside lip 5 tissues. The composition should be allowed to set for two (2) to three (3) minutes or until it is relatively firm. The shield 8 may then be removed from the mouth.

[1]Trademark of G-C Dental Industrial Corporation.

Figure 3:
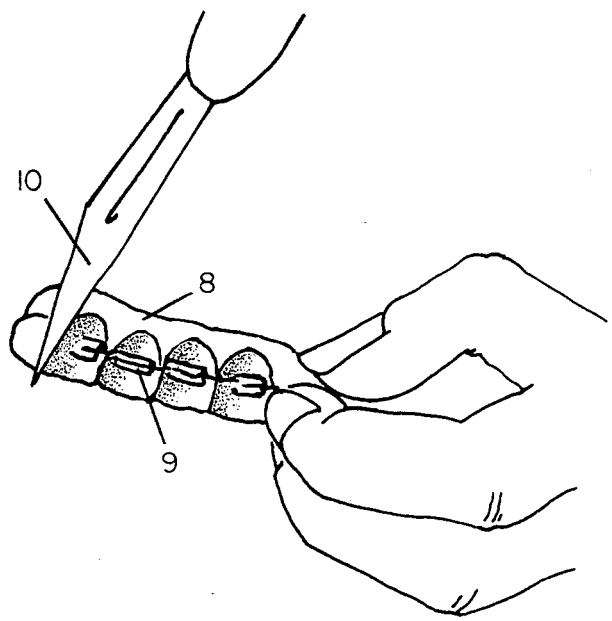
FIG. 3 shows the orthodontic shield being trimmed.
Figure 4:
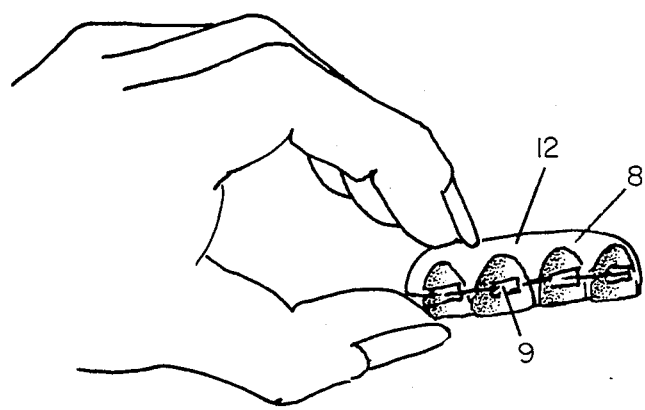
FIG. 4 is a side view of the shield after trimming, showing the surface which fits against the teeth and braces.
Figure 5:
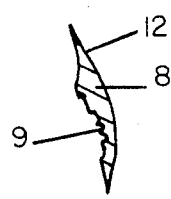
FIG. 5 is a fully sectioned view of the shield after trimming.
Figure 6:
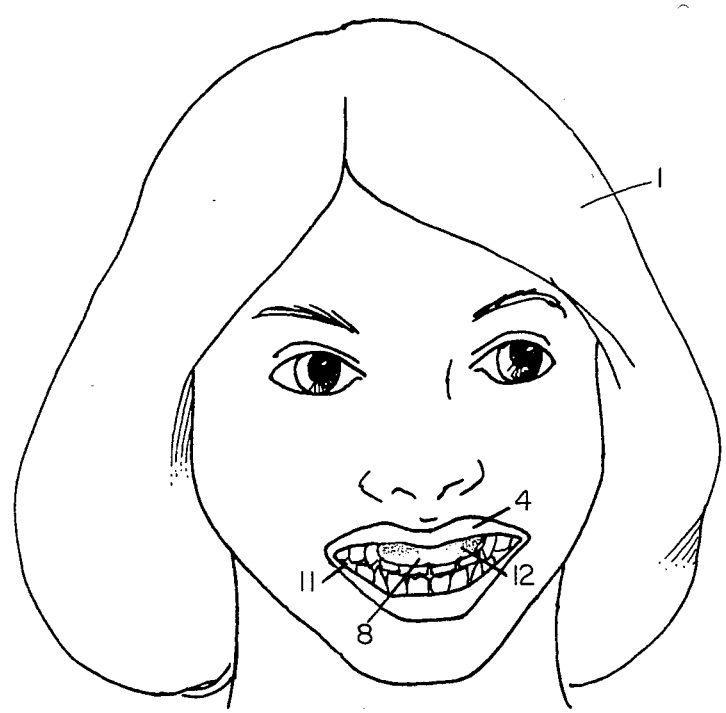
FIG. 6 is a view of the wearer of the shield, with the finished shield in place.

The shield 8 is removed from the mouth 11 by lifting one corner and peeling it back. As is shown in FIGS. 3, 4, and 5, the shield 8, after removal, will have indentions 9 which are formed exactly to the user's teeth 3, braces 2, lips 5, and gums 7. The shield 8 must now be trimmed, and this may be accomplished through the use of a knife, razor blade, or other sharp object 10, as in FIG. 4.

Figure 7:
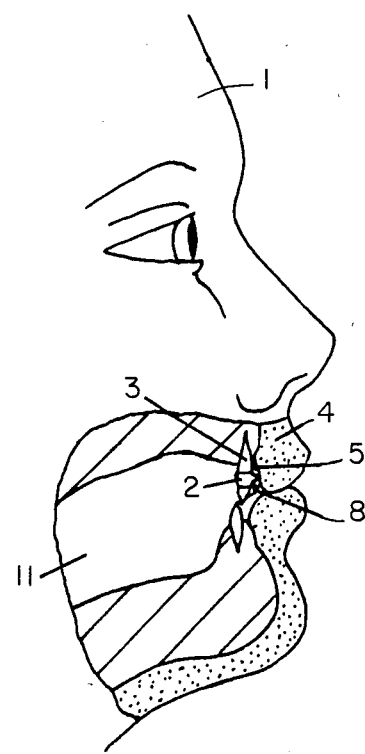
FIG. 7 is a partially sectioned view, showing the finished, trimmed shield in place in the wearer's mouth.

After trimming, the shield 8 should be reinserted into the user's mouth 11. The indentions 9 in the shield 8 from the braces 2 and teeth 3 will fit against the braces 2 and teeth 3, holding the shield 8 in place. The surfaces 12 of the shield 8 should be trimmed so that they are smooth, and the shield 8 should not extend below the teeth 3, to avoid interfering with the air flow, as shown in FIG. 7. The shield 8 should completely cover the braces 2 and be of a thickness which will shield the braces 2 from the inside of the lip 5, but which will not be so thick as to displace the upper lip 4, which would interfer with lip vibrations during playing of the musical instrument.

The shield 8 may be removed after use, and reused at a later time. Assuming proper, sanitary storage of the shield, such as in a small plastic bottle, the shield may last for more than three (3) months. The shield will not deform, and may be replaced in the user's mouth several times, each time aligning with the particular indentions or impressions in the shield created by the braces and teeth of the user in the material while the material is setting.

This method may be used generally as described above to produce a shield for use with linqual appliances. By applying the medical silicone to the inside of the teeth where the linqual appliance is located and following the same steps, a shield is produced which will protect the tongue from cuts, abrasions, and injury.

Figure 8:
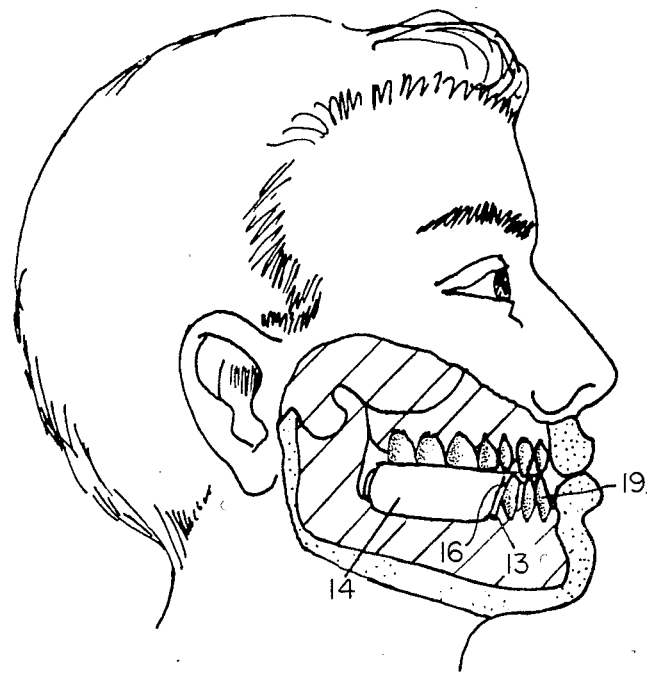
FIG. 8 is a partially sectioned view, showing the orthotic device in place as used to relieve temporomandibular joint syndrome.
Figure 9:
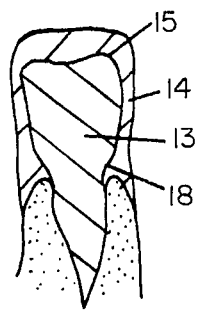
FIG. 9 is a sectioned view of a tooth and gum with the orthotic device in place.
Figure 10:
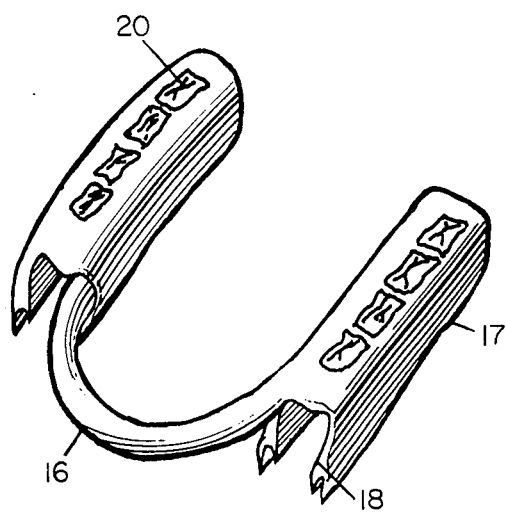
FIG. 10 is a perspective view of the completed view of the orthotic device.

A second preferred embodiment deals with the use of medical silicone to relieve temporomandibular joint syndrome. A room temperature setting medical silicone, as described above, is used. The two parts are mixed together thoroughly, and then placed on the most rearwardly located three or four lower teeth 13 on both sides, as shown in FIG. 8. A sufficient amount to completely cover the teeth completely is used. The medical silicone 14 should be of a sufficient thickness on the upper surface of the teeth 15 to hold the upper and lower teeth apart approximately one-eighth ($\frac{1}{8}$) inch (2–4 mm), as shown in FIG. 9. An additional strip 16 of the medical silicone 14 may be used to connect the two sides (left and right), so that when the medical silicone dries and is removed from the mouth, it is in one piece rather than two (FIG. 10). This additional strip is positioned on the inside of the lower teeth so as to not cover the lower front teeth 19 of the user.

The medical silicone 14 composition is allowed to set for two or three minutes, or until it is relatively firm. The orthotic device 17 is then removed from the mouth and may be trimmed by the use of a knife or other sharp object so that it is comfortable to the wearer, without excessive bulk, and so that it does not obscure the lower front teeth 19. The undercut area or angle 18 of the lower back teeth 13 holds the orthotic device in place during use. Indentations 20 from the upper teeth during the setting phase provide positioning of the upper teeth relative to the lower teeth.

This orthotic device may be inexpensively prepared by the wearer, and may be reused. By holding the upper and lower teeth slightly apart, pressure is relieved from the temporomandibular joint and strain is released from supporting muscles, resulting in relief from temporomandiular joint syndrome and associated problems.

The invention may be used with other orthodontic aids and appliances, such as the orthopedic head reposturing appliance (OHPA). Again, the room temperature setting medical silicone is prepared for use, and placed into the OHPA where the OHPA contacts the thin nose area on the face. After the medical silicone is allowed to set for 2 to 3 minutes, it is removed from the appliance. The medical silicone has formed precisely to the face of the user, and the excess medical silicone may be trimmed away. It is then replaced in the appliance and provides a cushion between the appliance, which applies great pressure to the face at the thin nose area, resulting in increased comfort to the wearer of the OHPA.

The preferred embodiments are given by way of description and not by way of limitation. The method of producing the shield and the shield may be used in conjunction with lower braces as well as upper braces, and with other forms and types of orthodontic aids. The shield may be used by non-wearers of orthodontic aids to shield oral irritations such as cuts, abrasions, herpes, ulcers, and other sores from further irritation by the teeth and other parts of the mouth.

What is claimed is:

1. A method of producing an orthodontic shield for use as an embouchure aid to reduce or eliminate cuts, abrasions and/or irritations incurred by a wearer of braces or other orthodontic appliances while playing a wind instrument, comrising:
   a. placing a quantity of medical silicone composition over teeth, braces, orthodontic appliances and other sources of oral irritations;

b. allowing said silicone to set and form so as to leave an impression in said silicone shaped by said teeth, braces, or orthodontic appliances;

c. removing said silicone from said wearer's mouth;

d. trimming said silicone to a size and shape which will protect said wearer's lips, gums and mouth tissue from said braces, orthodontic appliances or other sources of oral irritation while not impairing movement or vibration of said lips, gums or mouth tissue during the playing of said wind instrument; and e. placing said silicone into said wearer's mouth with said silicone being held in place by said braces or other orthodontic appliances fitting into said impression in said silicone.

2. A method of producing an orthodontic shield as described in claim 1, wherein said medical silicone is a polyvinyl silicone.

3. An orthodontic shield produced by the method described in claim 2.

4. A method of producing an orthodontic shield as described in claim 1, wherein said medical silicone is a composition comprising organovinylpolysiloxane, an organohydrogen polysiloxane, a catalyst for promoting an addition reaction therebetween, hydrophobic fillers and finely divided paladium and/or an alloy thereof, and wherein said organohydrogen polysiloxane and catalyst are homogeneously mixed just prior to placing said composition in said wearer's mouth.

5. An orthodontic shield produced by the method described in claim 4.

6. An orthodontic shield produced by the method described in claim 1.

7. A method of producing an orthotic device which may be used prophylactically, diagnostically and therapeutically in the treatment of temporomandibular joint syndrome and which may be prepared by the user, comprising:

a. placing a medical silicone composition into said wearer's mouth and over said wearer's lower set of teeth so as to cover three or four rearward most teeth on each side of said wearer's mouth, shaping said silicone so as to leave an impression from said teeth in said silicone;

b. allowing said medical silicone to set;

c. removing said medical silicone from said wearer's mouth;

d. trimming said silicone so as to leave silicone in sufficient thickness to hold said lower teeth and upper teeth apart approximately 2 to 4 millimeters and reduce pressure on the temporomandibular joint; and e. placing said silicone into said wearer's mouth so that said impressions in said silicone hold said silicone in place on said teeth.

8. A method of producing an orthotic device as described in claim 7, wherein said medical silicone is a polyvinyl silicone.

9. An orthotic device which may be used in the treatment of temporomandibular joint syndrome produced by the method described in claim 8.

10. An orthotic device which may be used in the treatment of temporomandibular joint syndrome produced by the method described in claim 1.

11. A method of producing an orthotic device as described in claim 1, wherein said medical silicone is a composition comprising organovinylpolysiloxane, an organohydrogen polysiloxane, a catalyst for promoting an addition reaction therebetween, hydrophobic fillers and finely divided paladium and/or an alloy thereof, and wherein said organohydrogen polysiloxane and catalyst are homogeneously mixed just prior to placing said composition in said wearer's mouth.

12. An orthotic device which may be used in the treatment of temporomandibular joint syndrome produced by the method described in claim 1.

* * * * *